(12) United States Patent
Von Oepen et al.

(10) Patent No.: US 7,794,491 B2
(45) Date of Patent: *Sep. 14, 2010

(54) APPARATUS FOR A STENT HAVING AN EXPANDABLE WEB STRUCTURE AND DELIVERY SYSTEM

(75) Inventors: Randolf Von Oepen, Los Altos Hills, CA (US); Gerd Seibold, Ammerbuch (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 937 days.

This patent is subject to a terminal disclaimer.

(21) Appl. No.: 10/903,014

(22) Filed: Jul. 30, 2004

(65) Prior Publication Data

US 2005/0004650 A1  Jan. 6, 2005

Related U.S. Application Data

(63) Continuation of application No. 10/743,857, filed on Dec. 22, 2003, which is a continuation of application No. 09/742,144, filed on Dec. 19, 2000, now Pat. No. 6,682,554, which is a continuation-in-part of application No. 09/582,318, filed as application No. PCT/EP99/06456 on Sep. 2, 1999, now Pat. No. 6,602,285.

(30) Foreign Application Priority Data

Sep. 5, 1998 (DE) .................................. 19840645

(51) Int. Cl.
*A61F 2/06* (2006.01)
*A61M 29/00* (2006.01)

(52) U.S. Cl. ...................................... 623/1.15; 606/198
(58) Field of Classification Search ................ 623/1.15; 606/198, 108, 195
See application file for complete search history.

(56) References Cited

U.S. PATENT DOCUMENTS

| 4,473,252 A | 9/1984 | Martin, Jr. et al. |
| 4,475,972 A | 10/1984 | Wong |
| 4,580,568 A | 4/1986 | Gianturco |
| 4,738,740 A | 4/1988 | Pinchuk et al. |

(Continued)

FOREIGN PATENT DOCUMENTS

CA  2309079  11/2004

(Continued)

OTHER PUBLICATIONS

U.S. Appl. No. 60/637,495, filed Dec. 20, 2004, Fierens et al.

(Continued)

*Primary Examiner*—Vy Q Bui
(74) *Attorney, Agent, or Firm*—Workman Nydegger

(57) ABSTRACT

The present invention provides a stent comprising a tubular flexible body having a wall with a web structure that is expandable from a contracted delivery configuration to deployed configuration. The web structure comprises a plurality of neighboring web patterns, where each web patterns is composed of adjoining webs, and the web patterns are interconnected by transition sections. Each adjoining web comprises a central section interposed between two lateral sections to form concave or convex configurations. A delivery system for the stent is also provided.

22 Claims, 10 Drawing Sheets

U.S. PATENT DOCUMENTS

| | | | |
|---|---|---|---|
| 4,743,252 A | 5/1988 | Martin, Jr. et al. | |
| 4,759,757 A | 7/1988 | Pinchuk | |
| 4,800,882 A | 1/1989 | Gianturco | |
| 4,907,336 A | 3/1990 | Gianturco | |
| 5,015,253 A | 5/1991 | MacGregor | |
| 5,041,126 A | 8/1991 | Gianturco | |
| 5,059,211 A | 10/1991 | Stack et al. | |
| 5,102,417 A | 4/1992 | Palmaz | |
| 5,104,404 A | 4/1992 | Wolff | |
| 5,116,360 A | 5/1992 | Pinchuk et al. | |
| 5,122,154 A | 6/1992 | Rhodes | |
| 5,133,732 A | 7/1992 | Wiktor | |
| 5,147,370 A | 9/1992 | McNamara et al. | |
| 5,163,951 A | 11/1992 | Pinchuk et al. | |
| 5,171,262 A | 12/1992 | MacGregor | |
| 5,221,261 A | 6/1993 | Termin et al. | |
| 5,282,823 A | 2/1994 | Schwartz et al. | |
| 5,292,331 A | 3/1994 | Boneau | |
| 5,314,444 A | 5/1994 | Gianturco | |
| 5,370,683 A | 12/1994 | Fontaine | |
| 5,378,239 A | 1/1995 | Termin et al. | |
| 5,380,299 A | 1/1995 | Fearnot et al. | |
| 5,421,955 A | 6/1995 | Lau et al. | |
| 5,443,458 A | 8/1995 | Eury | |
| 5,443,496 A | 8/1995 | Schwartz et al. | |
| 5,449,373 A | 9/1995 | Pinchasik et al. | |
| 5,476,508 A | 12/1995 | Amstrup | |
| 5,496,277 A | 3/1996 | Termin et al. | |
| 5,514,154 A | 5/1996 | Lau et al. | |
| 5,527,354 A | 6/1996 | Fontaine et al. | |
| 5,556,414 A | 9/1996 | Turi | |
| 5,569,295 A | 10/1996 | Lam | |
| 5,591,197 A | 1/1997 | Orth et al. | |
| 5,591,224 A | 1/1997 | Schwartz et al. | |
| 5,593,417 A | 1/1997 | Rhodes | |
| 5,593,442 A | 1/1997 | Klein | |
| 5,603,721 A | 2/1997 | Lau et al. | |
| 5,609,606 A | 3/1997 | O'Boyle | |
| 5,628,788 A | 5/1997 | Pinchuk | |
| 5,630,829 A | 5/1997 | Lauterjung | |
| 5,632,772 A | 5/1997 | Alcime et al. | |
| 5,639,278 A | 6/1997 | Dereume et al. | |
| 5,649,952 A | 7/1997 | Lam | |
| 5,651,174 A | 7/1997 | Schwartz et al. | |
| 5,653,747 A | 8/1997 | Dereume | |
| 5,670,161 A | 9/1997 | Healy et al. | |
| 5,674,242 A | 10/1997 | Phan et al. | |
| 5,674,277 A | 10/1997 | Freitag | |
| 5,693,085 A | 12/1997 | Buirge et al. | |
| 5,693,278 A | 12/1997 | Dereume et al. | |
| 5,695,516 A | 12/1997 | Fischell et al. | |
| 5,697,971 A | 12/1997 | Fischell et al. | |
| 5,700,285 A | 12/1997 | Myers et al. | |
| 5,707,386 A | 1/1998 | Schnepp-Pesch et al. | |
| 5,707,388 A | 1/1998 | Lauterjung | |
| 5,709,703 A | 1/1998 | Lukic et al. | |
| 5,709,713 A | 1/1998 | Evans et al. | |
| 5,716,393 A | 2/1998 | Lindenberg et al. | |
| 5,723,003 A | 3/1998 | Winston et al. | |
| 5,723,004 A | 3/1998 | Dereume et al. | |
| 5,728,158 A | 3/1998 | Lau et al. | |
| 5,733,303 A | 3/1998 | Israel et al. | |
| 5,735,892 A | 4/1998 | Myers et al. | |
| 5,735,893 A | 4/1998 | Lau et al. | |
| 5,735,897 A | 4/1998 | Buirge | |
| 5,738,817 A | 4/1998 | Danforth et al. | |
| 5,741,325 A | 4/1998 | Chaikof et al. | |
| 5,741,327 A | 4/1998 | Frantzen | |
| 5,743,874 A | 4/1998 | Fischell et al. | |
| 5,749,880 A | 5/1998 | Banas et al. | |
| 5,755,771 A | 5/1998 | Penn et al. | |
| 5,755,772 A | 5/1998 | Evans et al. | |
| 5,755,774 A | 5/1998 | Pinchuk | |
| 5,755,781 A | 5/1998 | Jayaraman | |
| 5,769,884 A | 6/1998 | Solovay | |
| 5,776,161 A | 7/1998 | Globerman | |
| 5,776,181 A | 7/1998 | Lee et al. | |
| 5,776,183 A | 7/1998 | Kanesaka et al. | |
| 5,800,526 A | 9/1998 | Anderson et al. | |
| 5,807,404 A * | 9/1998 | Richter | 623/1.16 |
| 5,810,868 A | 9/1998 | Lashinski et al. | |
| 5,810,870 A | 9/1998 | Myers et al. | |
| 5,810,872 A | 9/1998 | Kanesaka et al. | |
| 5,814,063 A | 9/1998 | Freitag | |
| 5,817,126 A | 10/1998 | Imran | |
| 5,824,037 A | 10/1998 | Fogarty et al. | |
| 5,824,045 A * | 10/1998 | Alt | 623/1.15 |
| 5,824,048 A | 10/1998 | Tuch | |
| 5,824,054 A | 10/1998 | Khosravi et al. | |
| 5,824,059 A | 10/1998 | Wijay | |
| 5,827,321 A | 10/1998 | Roubin et al. | |
| 5,836,964 A | 11/1998 | Richter et al. | |
| 5,836,966 A | 11/1998 | St. Germain | |
| 5,843,120 A | 12/1998 | Israel et al. | |
| 5,843,158 A | 12/1998 | Lenker et al. | |
| 5,843,161 A | 12/1998 | Solovay | |
| 5,843,164 A | 12/1998 | Frantzen et al. | |
| 5,846,247 A | 12/1998 | Unsworth et al. | |
| 5,853,419 A | 12/1998 | Imran | |
| 5,855,598 A | 1/1999 | Pinchuk | |
| 5,855,600 A | 1/1999 | Alt | |
| 5,860,999 A | 1/1999 | Schnepp-Pesch et al. | |
| 5,861,027 A * | 1/1999 | Trapp | 623/1.15 |
| 5,868,781 A | 2/1999 | Killion | |
| 5,871,538 A | 2/1999 | Dereume | |
| 5,876,449 A | 3/1999 | Starck et al. | |
| 5,876,450 A | 3/1999 | Johlin, Jr. | |
| 5,895,406 A | 4/1999 | Gray et al. | |
| 5,897,589 A | 4/1999 | Cottenceau et al. | |
| 5,922,021 A * | 7/1999 | Jang | 623/1.15 |
| 5,928,248 A | 7/1999 | Acker | |
| 5,938,682 A | 8/1999 | Hojeibane et al. | |
| 5,948,018 A | 9/1999 | Dereume et al. | |
| 5,954,743 A | 9/1999 | Jang | |
| 5,968,091 A | 10/1999 | Pinchuk et al. | |
| 5,980,552 A | 11/1999 | Pinchasik et al. | |
| 5,984,965 A | 11/1999 | Knapp et al. | |
| 6,017,365 A | 1/2000 | Von Oepen | |
| 6,019,789 A | 2/2000 | Dinh et al. | |
| 6,027,526 A | 2/2000 | Limon et al. | |
| 6,033,433 A | 3/2000 | Ehr et al. | |
| 6,033,434 A | 3/2000 | Borghi | |
| 6,033,435 A | 3/2000 | Penn et al. | |
| 6,039,756 A | 3/2000 | Jang | |
| 6,048,361 A | 4/2000 | Von Oepen | |
| 6,059,811 A | 5/2000 | Pinchasik et al. | |
| 6,068,656 A | 5/2000 | Von Oepen | |
| 6,071,308 A * | 6/2000 | Ballou et al. | 623/1.15 |
| 6,086,610 A | 7/2000 | Duerig et al. | |
| 6,099,561 A | 8/2000 | Alt | |
| 6,106,548 A | 8/2000 | Roubin et al. | |
| 6,113,627 A | 9/2000 | Jang | |
| 6,117,165 A * | 9/2000 | Becker | 623/1.15 |
| 6,117,535 A | 9/2000 | Szycher et al. | |
| 6,123,721 A * | 9/2000 | Jang | 623/1.15 |
| 6,132,460 A | 10/2000 | Thompson | |
| 6,165,212 A | 12/2000 | Dereume et al. | |
| 6,174,326 B1 | 1/2001 | Kitaoka et al. | |
| 6,179,868 B1 * | 1/2001 | Burpee et al. | 623/1.17 |
| 6,190,403 B1 * | 2/2001 | Fischell et al. | 623/1.16 |
| 6,193,744 B1 * | 2/2001 | Ehr et al. | 623/1.15 |
| 6,193,747 B1 * | 2/2001 | von Oepen | 623/1.15 |
| 6,200,334 B1 * | 3/2001 | Jang | 606/198 |
| 6,200,335 B1 | 3/2001 | Igaki | |

| | | | | | | |
|---|---|---|---|---|---|---|
| 6,203,569 B1 | 3/2001 | Wijay | | 2003/0055487 A1 | 3/2003 | Calisse |
| 6,231,598 B1 | 5/2001 | Berry et al. | | 2003/0083736 A1 | 5/2003 | Brown et al. |
| 6,231,600 B1 * | 5/2001 | Zhong ............... 623/1.42 | | 2003/0114918 A1 | 6/2003 | Garrison et al. |
| 6,241,762 B1 * | 6/2001 | Shanley ............... 623/1.17 | | 2003/0120334 A1 | 6/2003 | Gerbeding |
| 6,253,443 B1 | 7/2001 | Johnson | | 2004/0051201 A1 | 3/2004 | Greenhalgh et al. |
| 6,258,116 B1 * | 7/2001 | Hojeibane ............ 623/1.16 | | 2004/0093073 A1 | 5/2004 | Lowe et al. |
| 6,261,318 B1 | 7/2001 | Lee et al. | | 2004/0102836 A1 | 5/2004 | Fischell et al. |
| 6,264,688 B1 * | 7/2001 | Herklotz et al. ...... 623/1.16 | | 2004/0126405 A1 | 7/2004 | Sahatjian et al. |
| 6,264,690 B1 | 7/2001 | Von Oepen | | 2004/0193250 A1 | 9/2004 | Von Oepen et al. |
| 6,270,524 B1 | 8/2001 | Kim | | 2004/0230293 A1 | 11/2004 | Yip et al. |
| 6,273,913 B1 | 8/2001 | Wright et al. | | 2004/0236407 A1 | 11/2004 | Fierens et al. |
| 6,299,604 B1 | 10/2001 | Ragheb et al. | | 2004/0243220 A1 | 12/2004 | Gianotti et al. |
| 6,299,635 B1 * | 10/2001 | Frantzen ............... 623/1.17 | | 2005/0004651 A1 | 1/2005 | Von Oepen et al. |
| 6,325,825 B1 | 12/2001 | Kula et al. | | 2005/0004655 A2 | 1/2005 | Von Oepen et al. |
| 6,331,189 B1 | 12/2001 | Wolinsky et al. | | 2005/0004658 A1 | 1/2005 | Oepen et al. |
| 6,332,089 B1 | 12/2001 | Acker et al. | | 2005/0004659 A1 | 1/2005 | Von Oepen et al. |
| 6,340,366 B2 | 1/2002 | Wijay | | 2005/0004662 A1 | 1/2005 | Von Oepen et al. |
| 6,348,065 B1 | 2/2002 | Brown et al. | | 2005/0043777 A1 | 2/2005 | Von Oepen et al. |
| 6,377,835 B1 | 4/2002 | Schoenberg et al. | | 2005/0043778 A1 | 2/2005 | Von Oepen et al. |
| 6,395,020 B1 * | 5/2002 | Ley et al. ............... 623/1.15 | | 2005/0075716 A1 | 4/2005 | Yan |
| 6,436,132 B1 | 8/2002 | Patel et al. | | 2005/0222671 A1 | 10/2005 | Schaeffer et al. |
| 6,451,049 B2 | 9/2002 | Vallana et al. | | 2006/0015173 A1 | 1/2006 | Clifford et al. |
| 6,485,508 B1 | 11/2002 | McGuinness | | 2006/0106452 A1 | 5/2006 | Niermann |
| 6,488,702 B1 | 12/2002 | Besselink | | 2006/0142844 A1 | 6/2006 | Lowe et al. |
| 6,491,718 B1 | 12/2002 | Ahmad | | 2006/0175727 A1 | 8/2006 | Fierens et al. |
| 6,503,272 B2 | 1/2003 | Duerig et al. | | 2006/0184232 A1 | 8/2006 | Gianotti et al. |
| 6,506,211 B1 | 1/2003 | Skubitz et al. | | 2006/0206195 A1 | 9/2006 | Calisse |
| 6,508,834 B1 | 1/2003 | Pinchasik et al. | | 2006/0247759 A1 | 11/2006 | Burpee et al. |
| 6,540,776 B2 | 4/2003 | Sanders Millare et al. | | 2007/0021827 A1 | 1/2007 | Lowe et al. |
| 6,558,415 B2 | 5/2003 | Thompson | | 2007/0021834 A1 | 1/2007 | Young et al. |
| 6,572,646 B1 | 6/2003 | Boylan et al. | | 2007/0135891 A1 | 6/2007 | Schneider |
| 6,589,276 B2 | 7/2003 | Pinchasik et al. | | 2007/0179593 A1 | 8/2007 | Fierens et al. |
| 6,607,554 B2 | 8/2003 | Dang et al. | | 2007/0179601 A1 | 8/2007 | Fierens et al. |
| 6,616,689 B1 | 9/2003 | Ainsworth et al. | | 2007/0213800 A1 | 9/2007 | Fierens et al. |
| 6,624,097 B2 | 9/2003 | Martin et al. | | 2007/0299505 A1 | 12/2007 | Gregorich et al. |
| D481,139 S | 10/2003 | Seibold et al. | | 2008/0294239 A1 | 11/2008 | Casey |
| 6,629,994 B2 | 10/2003 | Gomez et al. | | 2008/0294240 A1 | 11/2008 | Casey |
| 6,679,911 B2 | 1/2004 | Burgermeister | | 2009/0163992 A1 | 6/2009 | Osman et al. |
| 6,723,119 B2 | 4/2004 | Pinchasik et al. | | 2009/0163996 A1 | 6/2009 | Bregulla |
| 6,730,252 B1 | 5/2004 | Teoh et al. | | 2009/0163997 A1 | 6/2009 | Casey |
| 6,740,114 B2 | 5/2004 | Burgermeister | | 2009/0163998 A1 | 6/2009 | Casey |
| 6,749,629 B1 | 6/2004 | Hong et al. | | | | |
| 6,755,856 B2 | 6/2004 | Fierens et al. | | | FOREIGN PATENT DOCUMENTS | |
| 6,776,794 B1 | 8/2004 | Hong et al. | | EP | 0699 451 | 3/1996 |
| 6,786,922 B2 | 9/2004 | Schaeffer | | EP | 0709067 | 5/1996 |
| 6,790,227 B2 | 9/2004 | Burgermeister | | EP | 0808614 | 11/1997 |
| 6,796,999 B2 | 9/2004 | Pinchasik | | EP | 0928605 | 7/1999 |
| 6,821,292 B2 | 11/2004 | Pazienza et al. | | EP | 0950386 | 10/1999 |
| 6,846,323 B2 | 1/2005 | Yip et al. | | EP | 0983753 | 3/2000 |
| 6,875,228 B2 | 4/2005 | Pinchasik et al. | | EP | 1042997 | 10/2000 |
| 6,881,222 B2 | 4/2005 | White et al. | | EP | 1095631 | 5/2001 |
| 6,913,619 B2 | 7/2005 | Brown et al. | | EP | 1516600 | 3/2005 |
| 6,916,336 B2 | 7/2005 | Patel et al. | | FR | 2774279 | 8/1999 |
| 6,929,660 B1 | 8/2005 | Ainsworth et al. | | GB | 2344 053 | 5/2000 |
| 6,942,689 B2 | 9/2005 | Majercak | | JP | 7-24072 | 1/1995 |
| 6,955,686 B2 | 10/2005 | Majercak et al. | | JP | 08-206226 | 8/1996 |
| 6,998,060 B2 | 2/2006 | Tomonto | | JP | 09-010318 | 1/1997 |
| 7,029,493 B2 | 4/2006 | Majercak et al. | | JP | 10-328216 | 12/1998 |
| 7,060,093 B2 | 6/2006 | Dang et al. | | JP | 11-299901 | 2/1999 |
| 7,128,756 B2 | 10/2006 | Lowe et al. | | JP | 200312721 | 11/2000 |
| 7,141,062 B1 | 11/2006 | Pinchasik et al. | | JP | 2000312721 | 11/2000 |
| 7,329,277 B2 | 2/2008 | Addonizio et al. | | WO | WO91/17789 | 11/1991 |
| 7,520,892 B1 | 4/2009 | Ainsworth et al. | | WO | WO9621404 | 7/1996 |
| 7,625,398 B2 | 12/2009 | Clifford et al. | | WO | WO96/25124 | 8/1996 |
| 2001/0027339 A1 | 10/2001 | Boatman et al. | | WO | WO 97/12563 | 4/1997 |
| 2001/0049549 A1 | 12/2001 | Boylan et al. | | WO | WO9712564 | 4/1997 |
| 2002/0019660 A1 | 2/2002 | Gianotti et al. | | WO | WO9714375 | 4/1997 |
| 2002/0035394 A1 | 3/2002 | Fierens et al. | | WO | WO9832412 | 7/1998 |
| 2002/0065549 A1 | 5/2002 | White et al. | | WO | WO98/47447 | 10/1998 |
| 2002/0107560 A1 | 8/2002 | Richter | | WO | WO9907308 | 2/1999 |
| 2002/0111669 A1 | 8/2002 | Pazienza et al. | | WO | WO99/17680 | 4/1999 |
| 2002/0151964 A1 | 10/2002 | Smith et al. | | WO | WO9923976 | 5/1999 |
| 2002/0169499 A1 | 11/2002 | Zilla et al. | | | | |

| | | |
|---|---|---|
| WO | WO99/38456 | 8/1999 |
| WO | WO99/38458 | 8/1999 |
| WO | WO 9939660 | 8/1999 |
| WO | WO99/49928 | 10/1999 |
| WO | WO0013611 | 3/2000 |
| WO | WO0032241 | 6/2000 |
| WO | WO0045744 | 8/2000 |
| WO | WO00/53119 | 9/2000 |
| WO | WO 01/01885 | 1/2001 |
| WO | WO01/82835 | 11/2001 |
| WO | WO02/26164 | 4/2002 |
| WO | WO02064061 | 8/2002 |
| WO | WO02064065 | 8/2002 |
| WO | WO02/094127 | 11/2002 |
| WO | WO03/009779 | 2/2003 |
| WO | WO03057076 | 7/2003 |
| WO | WO2004/087015 | 10/2004 |
| WO | WO2006/055533 | 5/2006 |
| WO | WO2006066886 | 6/2006 |
| WO | WO2006/099449 | 9/2006 |
| WO | WO2008/042618 | 4/2008 |
| WO | WO2008/142566 | 11/2008 |
| WO | WO2009/046973 | 4/2009 |

OTHER PUBLICATIONS

U.S. Appl. No. 09/582,318, mailed Aug. 14, 2002, Office Action.
U.S. Appl. No. 09/582,318, mailed Mar. 7, 2003, Notice of Allowance.
U.S. Appl. No. 09/582,318, mailed Jul. 17, 2003, Issue Notification.
U.S. Appl. No. 09/742,144, mailed Sep. 24, 2002, Office Action.
U.S. Appl. No. 09/742,144, mailed May 14, 2003, Office Action.
U.S. Appl. No. 09/742,144, mailed Aug. 29, 2003, Notice of Allowance.
U.S. Appl. No. 09/742,144, mailed Jan. 8, 2004, Issue Notification.
U.S. Appl. No. 09/916,394, mailed Mar. 2, 2004, Office Action.
U.S. Appl. No. 09/916,394, mailed Oct. 9, 2003, Office Action.
U.S. Appl. No. 09/916,394, mailed Aug. 12, 2003, Office Action.
U.S. Appl. No. 10/884,613, mailed Mar. 30, 2005, Office Action.
U.S. Appl. No. 10/884,613, mailed Nov. 14, 2005, Office Action.
U.S. Appl. No. 09/967,789, mailed Sep. 17, 2003, Office Action.
U.S. Appl. No. 09/967,789, mailed Feb. 17, 2004, Notice of Allowance.
U.S. Appl. No. 09/967,789, mailed Jun. 10, 2004, Issue Notification.
U.S. Appl. No. 10/859,636, mailed Jun. 1, 2007, Office Action.
U.S. Appl. No. 10/859,636, mailed Dec. 31, 2007, Office Action.
U.S. Appl. No. 10/859,636, mailed Oct. 1, 2008, Notice of Allowance.
U.S. Appl. No. 10/743,857, mailed Mar. 15, 2007, Office Action.
U.S. Appl. No. 10/743,857, mailed Nov. 16, 2007, Office Action.
U.S. Appl. No. 10/743,857, mailed May 8, 2008, Office Action.
U.S. Appl. No. 10/743,857, mailed Jan. 6, 2009, Office Action.
U.S. Appl. No. 10/903,013, mailed Mar. 15, 2007, Office Action.
U.S. Appl. No. 10/903,013, mailed Nov. 19, 2007, Office Action.
U.S. Appl. No. 10/903,013, mailed May 14, 2008, Office Action.
U.S. Appl. No. 10/903,013, mailed Jan. 5, 2009, Office Action.
U.S. Appl. No. 10/903,080, mailed Mar. 15, 2007, Office Action.
U.S. Appl. No. 10/903,080, mailed Nov. 19, 2007, Office Action.
U.S. Appl. No. 10/903,080, mailed May 12, 2008, Office Action.
U.S. Appl. No. 10/903,080, mailed Dec. 30, 2008, Office Action.
U.S. Appl. No. 10/909,117, mailed Aug. 22, 2007, Office Action.
U.S. Appl. No. 10/909,117, mailed May 12, 2008, Office Action.
U.S. Appl. No. 10/909,117, mailed Dec. 30, 2008, Office Action.
U.S. Appl. No. 10/909,118, mailed Mar. 29, 2007, Office Action.
U.S. Appl. No. 10/909,118, mailed Nov. 19, 2007, Office Action.
U.S. Appl. No. 10/909,118, mailed May 12, 2008, Office Action.
U.S. Appl. No. 10/909,118, mailed Jan. 5, 2009, Office Action.
U.S. Appl. No. 10/954,948, mailed Mar. 15, 2007, Office Action.
U.S. Appl. No. 10/954,948, mailed Nov. 16, 2007, Office Action.
U.S. Appl. No. 10/954,948, mailed May 15, 2008, Office Action.
U.S. Appl. No. 10/954,948, mailed Jan. 13, 2009, Office Action.
U.S. Appl. No. 10/955,425, mailed Mar. 15, 2007, Office Action.
U.S. Appl. No. 10/955,425, mailed Nov. 16, 2007, Office Action.
U.S. Appl. No. 10/955,425, mailed May 13, 2008, Office Action.
U.S. Appl. No. 10/955,425, mailed Jan. 13, 2009, Office Action.
U.S. Appl. No. 11/313,110, mailed Jan. 8, 2008, Office Action.
U.S. Appl. No. 11/313,110, mailed Jul. 2, 2008, Office Action.
U.S. Appl. No. 11/404,450, mailed Feb. 4, 2009, Office Action.
U.S. Appl. No. 11/404,450, mailed Mar. 17, 2009, Office Action.
U.S. Appl. No. 11/601,475, mailed Jul. 22, 2008, Office Action.
U.S. Appl. No. 11/601,475, mailed Jan. 6, 2009, Office Action.
U.S. Appl. No. 10/859,636, mailed Apr. 15, 2008, Office Action.
U.S. Appl. No. 10/859,636, mailed Mar. 5, 2009, Office Action.
U.S. Appl. No. 10/859,636, mailed Oct. 19, 2009, Notice of Allowance.
U.S. Appl. No. 10/743,857, mailed May 27, 2009, Office Action.
U.S. Appl. No. 10/903,013, mailed May 27, 2009, Office Action.
U.S. Appl. No. 10/903,080, mailed May 27, 2009, Office Action.
U.S. Appl. No. 10/909,117, mailed May 27, 2009, Office Action.
U.S. Appl. No. 10/909,118, mailed Jul. 24, 2009, Office Action.
U.S. Appl. No. 10/954,948, mailed May 29, 2009, Office Action.
U.S. Appl. No. 10/955,425, mailed May 28, 2009, Office Action.
U.S. Appl. No. 11/404,450, mailed Sep. 30, 2009, Office Action.
U.S. Appl. No. 11/601,475, mailed Jun. 1, 2009, Office Action.
U.S. Appl. No. 11/732,244, mailed Sep. 28, 2009, Office Action.
U.S. Appl. No. 10/241,523, filed Aug. 18, 2004, Office Action.
U.S. Appl. No. 10/241,523, filed Oct. 25, 2004, Office Action.
U.S. Appl. No. 10/241,523, filed Mar. 8, 2005, Office Action.
U.S. Appl. No. 10/241,523, filed Jun. 3, 2005, Office Action.
U.S. Appl. No. 10/241,523, filed Aug. 23, 2005, Office Action.
U.S. Appl. No. 10/241,523, filed Nov. 16, 2005, Office Action.
U.S. Appl. No. 10/241,523, filed Apr. 27, 2006, Office Action.
U.S. Appl. No. 10/743,857, filed Feb. 12, 2010, Notice of Allowance.
U.S. Appl. No. 10/859,636, filed Feb. 1, 2010, Notice of Allowance.
U.S. Appl. No. 10/903,013, filed Feb. 12, 2010, Notice of Allowance.
U.S. Appl. No. 10/903,080, filed Jan. 13, 2010, Notice of Allowance.
U.S. Appl. No. 10/909,117, filed Jan. 13, 2010, Notice of Allowance.
U.S. Appl. No. 10/909,118, filed Jan. 13, 2010, Notice of Allowance.
U.S. Appl. No. 10/954,948, filed Jan. 13, 2010, Notice of Allowance.
U.S. Appl. No. 10/955,425, filed Feb. 26, 2010, Notice of Allowance.
U.S. Appl. No. 11/313,110, filed Nov. 2, 2009, Notice of Allowance.
U.S. Appl. No. 11/435,260, filed Jan. 10, 2008, Office Action.
U.S. Appl. No. 11/435,260, filed Mar. 26, 2008, Office Action.
U.S. Appl. No. 11/435,260, filed Dec. 16, 2008, Office Action.
U.S. Appl. No. 11/435,260, filed Jun. 18, 2009, Notice of Allowance.
U.S. Appl. No. 11/435,260, filed Jun. 26, 2009, Notice of Allowance.
U.S. Appl. No. 11/601,475, filed Jan. 15, 2010, Notice of Allowance.
U.S. Appl. No. 11/731,820, filed Jan. 27, 2010, Office Action.
U.S. Appl. No. 11/731,882, filed Feb. 3, 2010, Office Action.
U.S. Appl. No. 11/805,584, filed Apr. 27, 2009, Office Action.
U.S. Appl. No. 11/805,584, filed Oct. 29, 2009, Office Action.
U.S. Appl. No. 11/805,584, filed Mar. 15, 2010, Office Action.
U.S. Appl. No. 11/961,290, filed May 6, 2009, Office Action.
U.S. Appl. No. 11/961,290, filed Dec. 18, 2009, Office Action.
U.S. Appl. No. 11/961,384, filed May 26, 2009, Office Action.
U.S. Appl. No. 11/961,384, filed Oct. 8, 2009, Office Action.
U.S. Appl. No. 11/961,754, filed Jul. 22, 2009, Office Action.
U.S. Appl. No. 11/973,707, filed Jun. 9, 2009, Office Action.
U.S. Appl. No. 11/973,707, filed Mar. 19, 2010, Office Action.
U.S. Appl. No. 11/404,450, filed Apr. 22, 2010, Office Action.
U.S. Appl. No. 11/961,754, filed Apr. 5, 2010, Notice of Allowance.
U.S. Appl. No. 11/732,244, filed May 5, 2010, Notice of Allowance.
U.S. Appl. No. 11/313,110, filed Feb. 18, 2010, Notice of Allowance.
U.S. Appl. No. 11/961,775, filed Oct. 1, 2009, Office Action.
U.S. Appl. No. 11/961,775, filed Mar. 31, 2010, Office Action.
U.S. Appl. No. 10/743,857, filed Jun. 25, 2010, Notice of Allowance.
U.S. Appl. No. 10/859,636, filed May 19, 2010, Notice of Allowance.
U.S. Appl. No. 10/903,013, filed Jun. 24, 2010, Notice of Allowance.
U.S. Appl. No. 10/955,425, filed Jun. 25, 2010, Notice of Allowance.
U.S. Appl. No. 11/732,244, filed Jun. 21, 2010, Notice of Allowance.

* cited by examiner

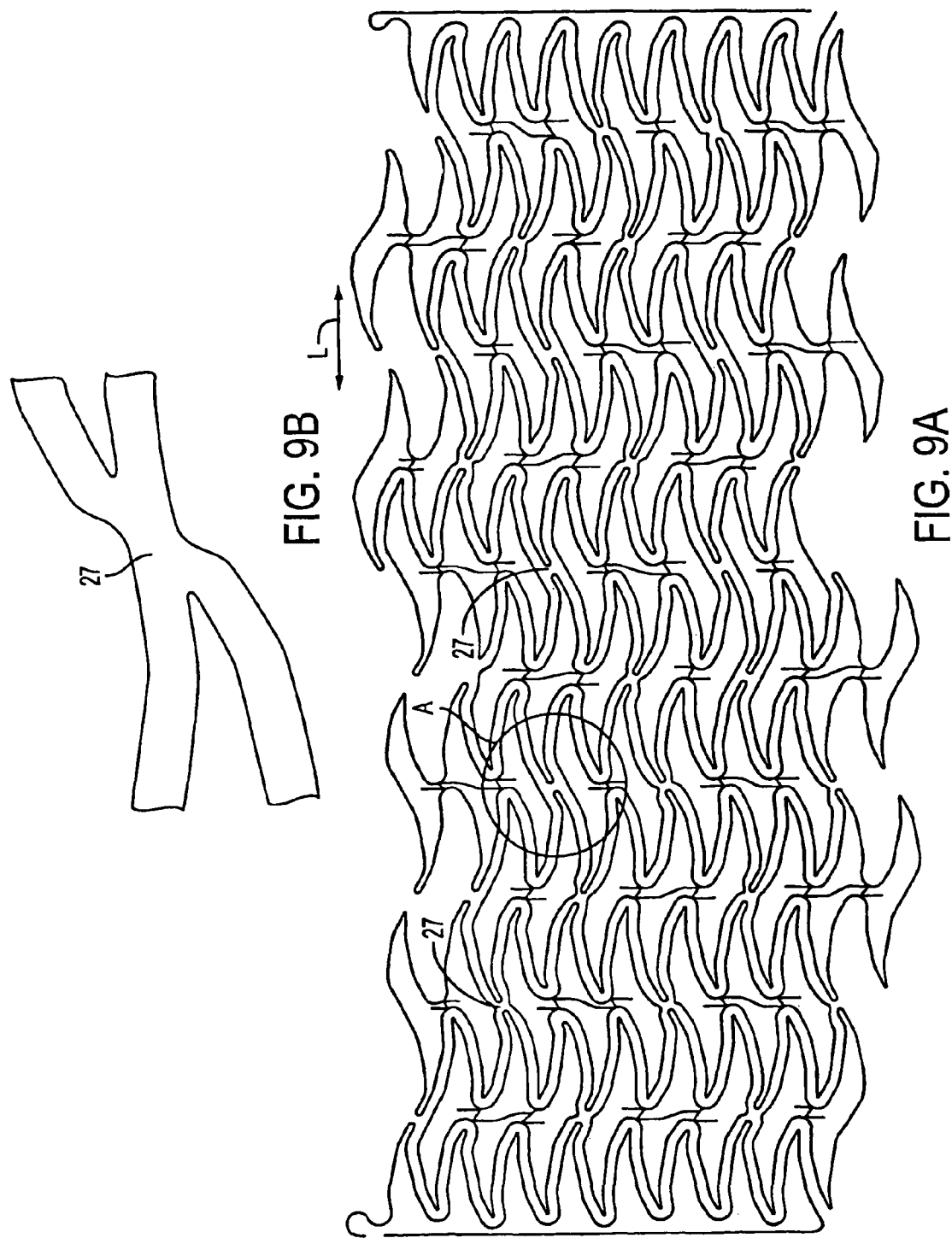

APPARATUS FOR A STENT HAVING AN EXPANDABLE WEB STRUCTURE AND DELIVERY SYSTEM

REFERENCE TO RELATED APPLICATIONS

The present application is a continuation application of U.S. patent application Ser. No. 10/743,857, filed Dec. 22, 2003, which is a continuation application of U.S. patent application Ser. No. 09/742,144, filed Dec. 19, 2000, now U.S. Pat. No. 6,682,554, which is a continuation-in-part application of U.S. patent application Ser. No. 09/582,318, filed Jun. 23, 2000, now U.S. Pat. No. 6,602,285, which claims the benefit of the filing date of International Application PCT/EP99/06456, filed Sep. 2, 1999, which claims priority from German application 19840645.2, filed Sep. 5, 1998, the entireties of which are incorporated herein by reference.

FIELD OF THE INVENTION

The present invention relates to stents. More particularly, the present invention relates to stents having a web structure configured to expand from a contracted delivery configuration to an expanded deployed configuration.

BACKGROUND OF THE INVENTION

Various stent designs are known in the art. These stents form vascular prostheses fabricated from biocompatible materials. Stents are typically used to expand and maintain patency of hollow vessels, such as blood vessels or other body orifices. To this end, the stent is often placed into a hollow vessel of a patient's body in a contracted delivery configuration and is subsequently expanded by suitable means, such as by a balloon catheter, to a deployed configuration.

A stent often comprises a stent body that is expandable from the contracted to the deployed configuration. A common drawback of such a stent is that the stent decreases in length, or foreshortens, along its longitudinal axis as it expands. Such shortening is undesirable because, in the deployed configuration, the stent may not span the entire area inside a vessel or orifice that requires expansion and/or support.

It therefore would be desirable to provide a stent that experiences reduced foreshortening during deployment.

It also would be desirable to provide a stent that is flexible, even in the contracted delivery configuration.

It would be desirable to provide a stent having radial stiffness in the expanded deployed configuration sufficient to maintain vessel patency in a stenosed vessel.

SUMMARY OF THE INVENTION

In view of the foregoing, it is an object of the present invention to provide a stent that experiences reduced foreshortening during deployment.

It is another object to provide a stent that is flexible, even in the contracted delivery configuration.

It is also an object to provide a stent having radial stiffness in the expanded deployed configuration sufficient to maintain vessel patency in a stenosed vessel.

These and other objects of the present invention are accomplished by providing a stent having a tubular body whose wall has a web structure configured to expand from a contracted delivery configuration to an expanded deployed configuration. The web structure comprises a plurality of neighboring web patterns having adjoining webs. Each web has three sections: a central section arranged substantially parallel to the longitudinal axis in the contracted delivery configuration, and two lateral sections coupled to the ends of the central section. The angles between the lateral sections and the central section increase during expansion, thereby reducing or substantially eliminating length decrease of the stent due to expansion, while increasing a radial stiffness of the stent.

Preferably, each of the three sections of each web is substantially straight, the lateral sections preferably define obtuse angles with the central section, and the three sections are arranged relative to one another to form a concave or convex structure. When contracted to its delivery configuration, the webs resemble stacked or nested bowls or plates. This configuration provides a compact delivery profile, as the webs are packed against one another to form web patterns resembling rows of stacked plates.

Neighboring web patterns are preferably connected to one another by connection elements preferably formed as straight sections. In a preferred embodiment, the connection elements extend between adjacent web patterns from the points of interconnection between neighboring webs within a given web pattern.

The orientation of connection elements between a pair of neighboring web patterns preferably is the same for all connection elements disposed between the pair. However, the orientation of connection elements alternates between neighboring pairs of neighboring web patterns. Thus, a stent illustratively flattened and viewed as a plane provides an alternating orientation of connection elements between the neighboring pairs: first upwards, then downwards, then upwards, etc.

As will be apparent to one of skill in the art, positioning, distribution density, and thickness of connection elements and adjoining webs may be varied to provide stents exhibiting characteristics tailored to specific applications. Applications may include, for example, use in the coronary or peripheral (e.g. renal) arteries. Positioning, density, and thickness may even vary along the length of an individual stent in order to vary flexibility and radial stiffness characteristics along the length of the stent.

Stents of the present invention preferably are flexible in the delivery configuration. Such flexibility beneficially increases a clinician's ability to guide the stent to a target site within a patient's vessel. Furthermore, stents of the present invention preferably exhibit high radial stiffness in the deployed configuration. Implanted stents therefore are capable of withstanding compressive forces applied by a vessel wall and maintain vessel patency. The web structure described hereinabove provides the desired combination of flexibility in the delivery configuration and radial stiffness in the deployed configuration. The combination further may be achieved, for example, by providing a stent having increased wall thickness in a first portion of the stent and decreased wall thickness with fewer connection elements in an adjacent portion or portions of the stent.

Depending on the material of fabrication, a stent of the present invention may be either self-expanding or expandable by other suitable means, for example, using a balloon catheter. Self-expanding embodiments preferably are fabricated from a superelastic material, such as a nickel-titanium alloy. Regardless of the expansion mechanism used, the beneficial aspects of the present invention are maintained: reduced shortening upon expansion, high radial stiffness, and a high degree of flexibility.

Methods of using stents in accordance with the present invention are also provided.

BRIEF DESCRIPTION OF THE DRAWINGS

The above and other objects and advantages of the present invention will be apparent upon consideration of the following detailed description, taken in conjunction with the accompanying drawings, in which like reference numerals refer to like parts throughout, and in which:

FIGS. 9A and 9B are, respectively, a schematic and detailed view of yet another alternative embodiment of the web structure of FIG. 5.

DETAILED DESCRIPTION OF THE INVENTION

Figure 1:
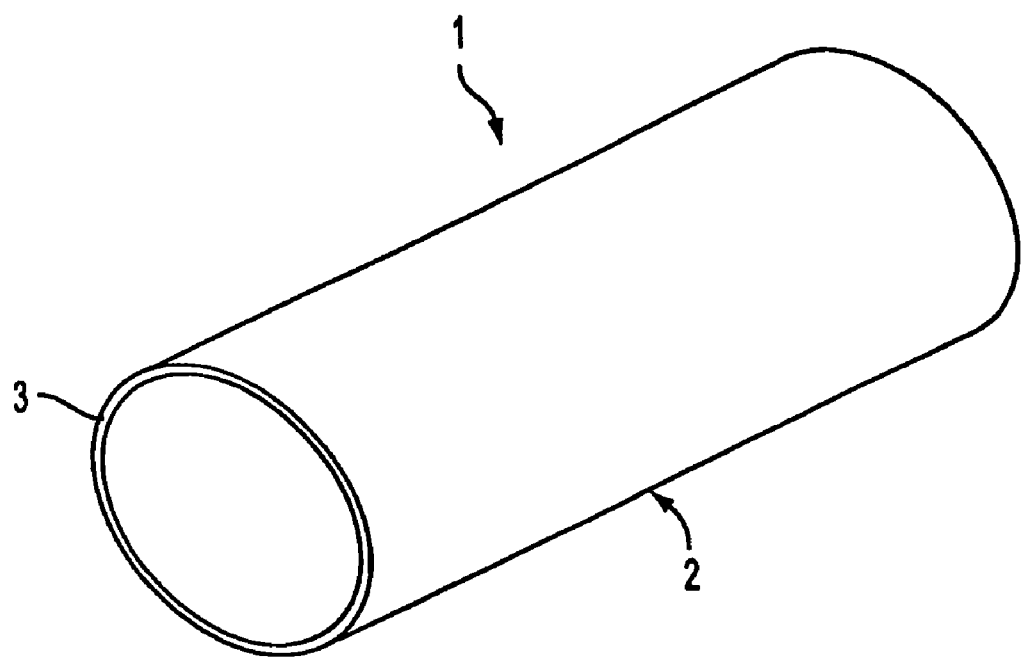
FIG. 1 is a schematic isometric view illustrating the basic structure of a stent according to the present invention.

Referring to FIG. 1, stent 1 comprises tubular flexible body 2. Tubular flexible body 2, in turn, comprises wall 3 having a web structure, as described hereinbelow with respect to FIGS. 2-9. Stent 1 and its web structure are expandable from a contracted delivery configuration to an expanded deployed configuration. Depending on the material of fabrication, stent 1 may be either self-expanding or expandable using a balloon catheter. If self-expanding, the web structure is preferably fabricated from a superelastic material, such as a nickel-titanium alloy. Furthermore, stent 1 preferably is fabricated from biocompatible or biodegradable materials. It also may be radiopaque to facilitate delivery, and it may comprise an external coating C that retards thrombus formation or restenosis within a vessel. The coating alternatively may deliver therapeutic agents into the patient's blood stream.

Figure 2:
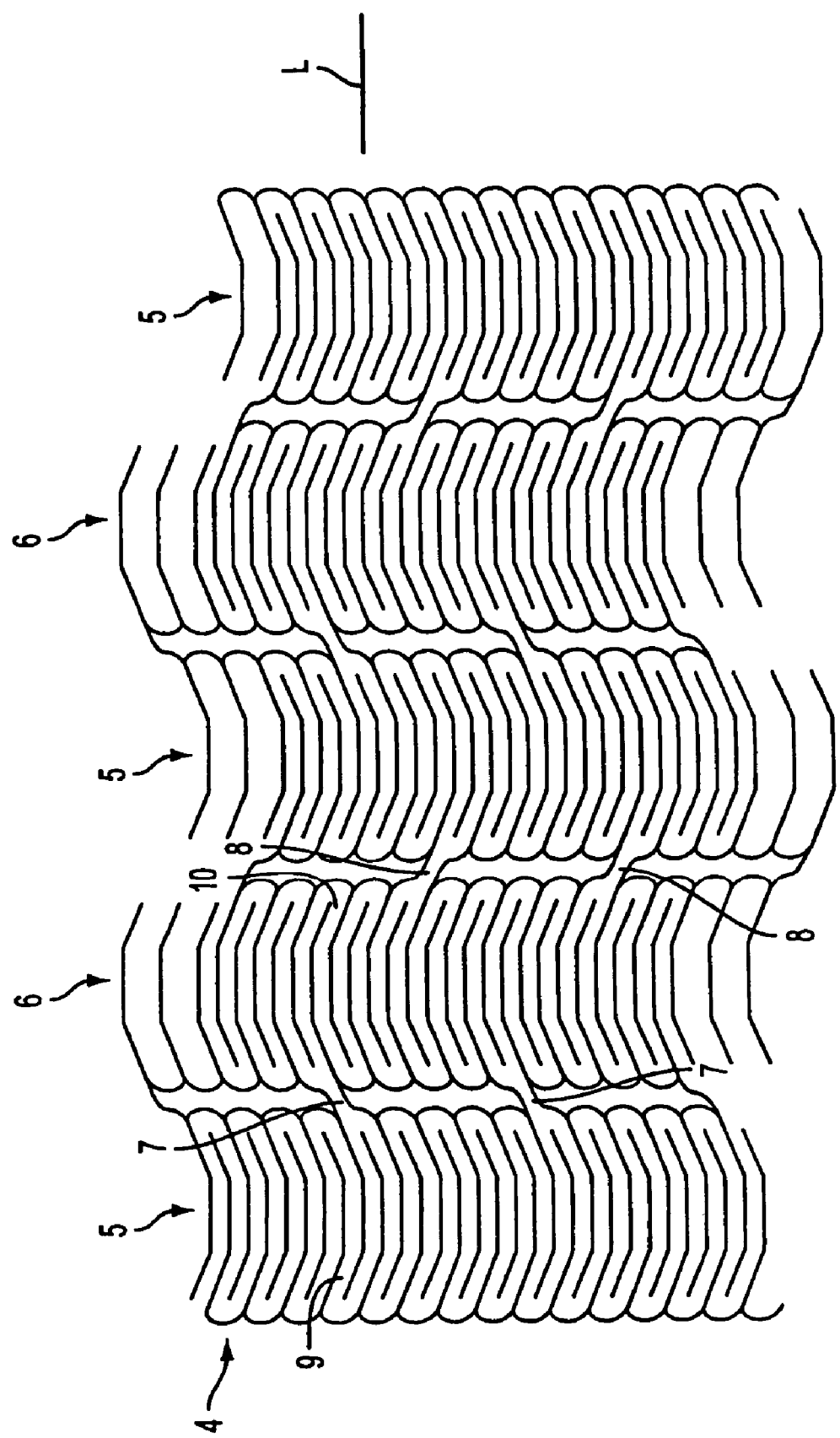
FIG. 2 is a schematic view illustrating a web structure of a wall of the stent of FIG. 1 in a contracted delivery configuration.
Figure 3:
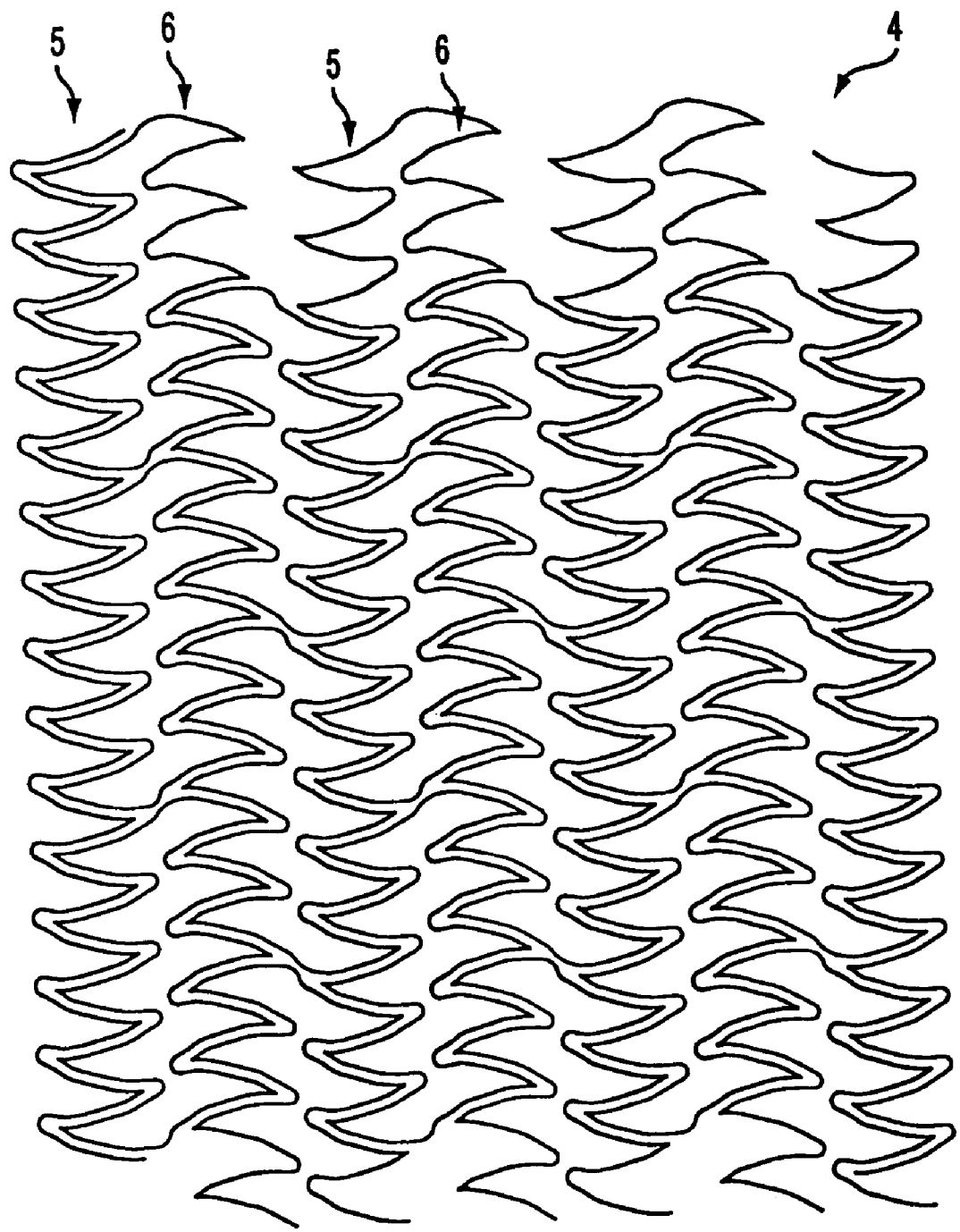
FIG. 3 is a schematic view illustrating the web structure of the stent of FIG. 1 in an expanded deployed configuration.
Figure 4:
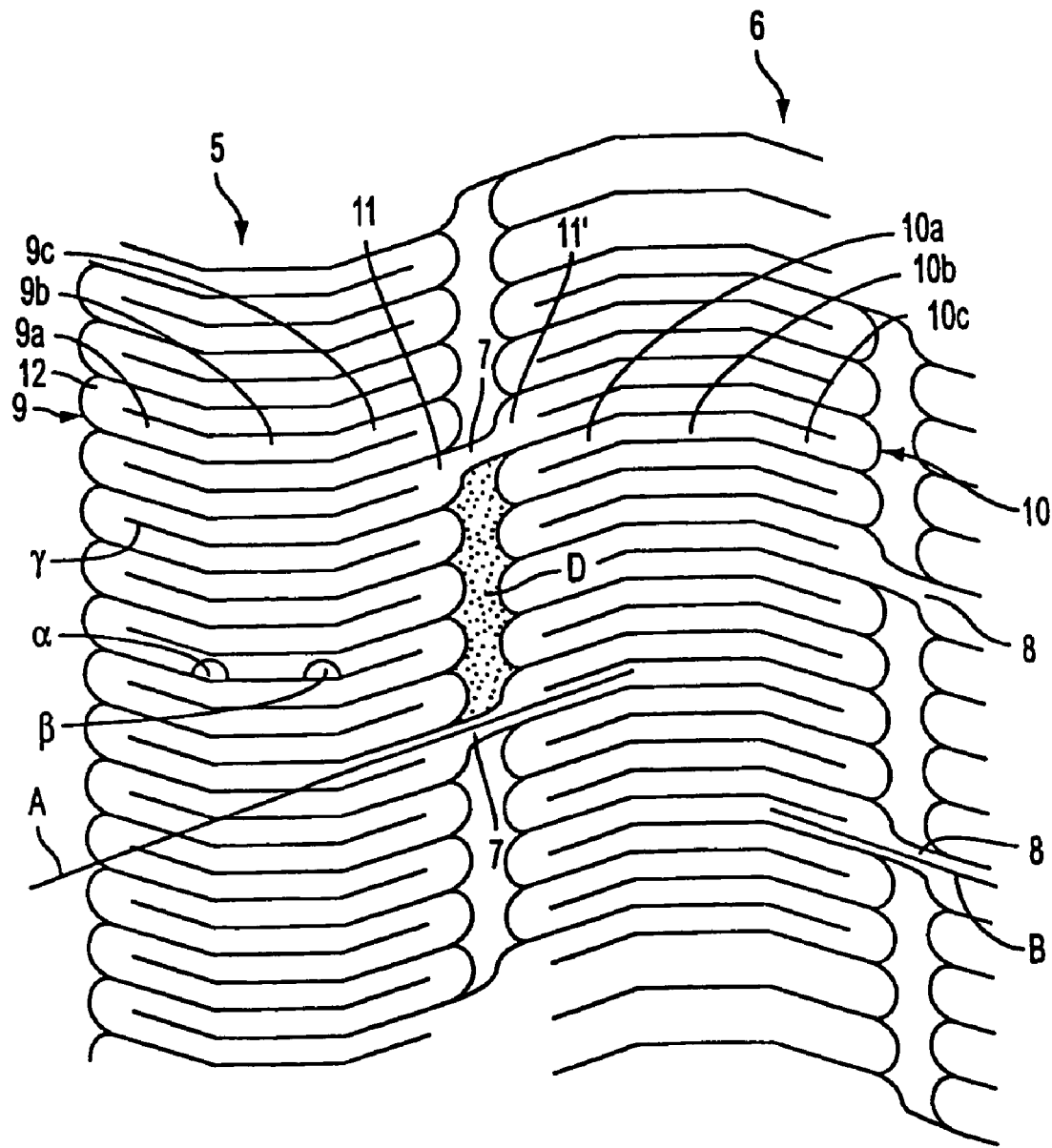
FIG. 4 is an enlarged schematic view of the web structure in the delivery configuration.

With reference to FIGS. 2-4, a first embodiment of the web structure of stent 1 is described. In FIGS. 2-4, wall 3 of body 2 of stent 1 is shown flattened into a plane for illustrative purposes. FIG. 2 shows web structure 4 in a contracted delivery configuration, with line L indicating the longitudinal axis of the stent. Web structure 4 comprises neighboring web patterns 5 and 6 arranged in alternating, side-by-side fashion. Thus, the web patterns seen in FIG. 2 are arranged in the sequence 5, 6, 5, 6, 5, etc.

FIG. 2 illustrates that web patterns 5 comprise adjoining webs 9 (concave up in FIG. 2), while web patterns 6 comprise adjoining webs 10 (convex up in FIG. 2). Each of these webs has a concave or convex shape resulting in a stacked plate- or bowl-like appearance when the stent is contracted to its delivery configuration. Webs 9 of web patterns 5 are rotated 180 degrees with respect to webs 10 of web patterns 6, i.e., alternating concave and convex shapes. The structure of webs 9 and 10 is described in greater detail hereinbelow with respect to FIG. 4.

Neighboring web patterns 5 and 6 are interconnected by connection elements 7 and 8. A plurality of connection elements 7 and 8 are provided longitudinally between each pair of web patterns 5 and 6. Multiple connection elements 7 and 8 are disposed in the circumferential direction between adjacent webs 5 and 6. The position, distribution density, and thickness of these pluralities of connection elements may be varied to suit specific applications in accordance with the present invention.

Connection elements 7 and 8 exhibit opposing orientation. However, all connection elements 7 have the same orientation that, as seen in FIG. 2, extends from the left side, bottom, to the right side, top. Likewise, all connection elements 8 have the same orientation that extends from the left side, top, to the right side, bottom. Connection elements 7 and 8 alternate between web patterns 5 and 6, as depicted in FIG. 2.

FIG. 3 illustrates the expanded deployed configuration of stent 1, again with reference to a portion of web structure 4. When stent 1 is in the expanded deployed configuration, web structure 4 provides stent 1 with high radial stiffness. This stiffness enables stent 1 to remain in the expanded configuration while, for example, under radial stress. Stent 1 may experience application of radial stress when, for example, implanted into a hollow vessel in the area of a stenosis.

FIG. 4 is an enlarged view of web structure 4 detailing a portion of the web structure disposed in the contracted delivery configuration of FIG. 2. FIG. 4 illustrates that each of webs 9 of web pattern 5 comprises three sections 9a, 9b and 9c, and each of webs 10 of web pattern 6 comprises three sections 10a, 10b and 10c. Preferably, each individual section 9a, 9b, 9c, 10a, 10b and 10c, has a straight configuration.

Each web 9 has a central section 9b connected to lateral sections 9a and 9c, thus forming the previously mentioned bowl- or plate-like configuration. Sections 9a and 9b enclose obtuse angle $\alpha$. Likewise, central section 9b and lateral section 9c enclose obtuse angle $\beta$. Sections 10a-10c of each web 10 of each web pattern 6 are similarly configured, but are rotated 180 degrees with respect to corresponding webs 9. Where two sections 9a or 9c, or 10a or 10c adjoin one another, third angle $\gamma$ is formed (this angle is zero where the stent is in the fully contracted position, as shown in FIG. 4).

Preferably, central sections 9b and 10b are substantially aligned with the longitudinal axis L of the tubular stent when the stent is in the contracted delivery configuration. The angles between the sections of each web increase in magnitude during expansion to the deployed configuration, except that angle $\gamma$, which is initially zero or acute, approaches a right angle after deployment of the stent. This increase provides high radial stiffness with reduced shortening of the stent length during deployment. As will of course be understood by one of ordinary skill, the number of adjoining webs that span a circumference of the stent preferably is selected corresponding to the vessel diameter in which the stent is intended to be implanted.

FIG. 4 illustrates that, with stent 1 disposed in the contracted delivery configuration, webs 9 adjoin each other in an alternating fashion and are each arranged like plates stacked into one another, as are adjoining webs 10. FIG. 4 further illustrates that the configuration of the sections of each web applies to all of the webs which jointly form web structure 4 of wall 3 of tubular body 2 of stent 1. Webs 9 are interconnected within each web pattern 5 via rounded connection sections 12, of which one connection section 12 is representatively labeled. Webs 10 of each neighboring web pattern 6 are similarly configured.

FIG. 4 also once again demonstrates the arrangement of connection elements 7 and 8. Connection elements 7, between a web pattern 5 and a neighboring web pattern 6, are disposed obliquely relative to the longitudinal axis L of the stent with an orientation A, which is the same for all connection elements 7. Orientation A is illustrated by a straight line that generally extends from the left side, bottom, to the right side, top of FIG. 4. Likewise, the orientation of all connection elements 8 is illustrated by line B that generally extends from the left side, top, to the right side, bottom of FIG. 4. Thus, an alternating A, B, A, B, etc., orientation is obtained over the entirety of web structure 4 for connection elements between neighboring web patterns.

Connection elements 7 and 8 are each configured as a straight section that passes into a connection section 11 of web pattern 5 and into a connection section 11' of web pattern 6. This is illustratively shown in FIG. 4 with a connection element 7 extending between neighboring connection sections 11 and 11', respectively. It should be understood that this represents a general case for all connection elements 7 and 8.

Since each web consists of three interconnected sections that form angles $\alpha$ and $\beta$ with respect to one another, which angles are preferably obtuse in the delivery configuration, expansion to the deployed configuration of FIG. 3 increases the magnitude of angles $\alpha$ and $\beta$. This angular increase beneficially provides increased radial stiffness in the expanded configuration. Thus, stent 1 may be flexible in the contracted delivery configuration to facilitate delivery through tortuous anatomy, and also may exhibit sufficient radial stiffness in the expanded configuration to ensure vessel patency, even when deployed in an area of stenosis. The increase in angular magnitude also reduces and may even substantially eliminate length decrease of the stent due to expansion, thereby decreasing a likelihood that stent 1 will not completely span a target site within a patient's vessel post-deployment.

The stent of FIG. 4 is particularly well-suited for use as a self-expanding stent when manufactured, for example, from a shape memory alloy such as nickel-titanium. In this case, web patterns 5 and 6 preferably are formed by laser-cutting a tubular member, wherein adjacent webs 9 and 10 are formed using slit-type cuts. Only the areas circumferentially located between connection members 7 and 8 (shaded area D in FIG. 4) require removal of areas of the tubular member. These areas also may be removed from the tubular member using laser cutting techniques.

Figure 5:
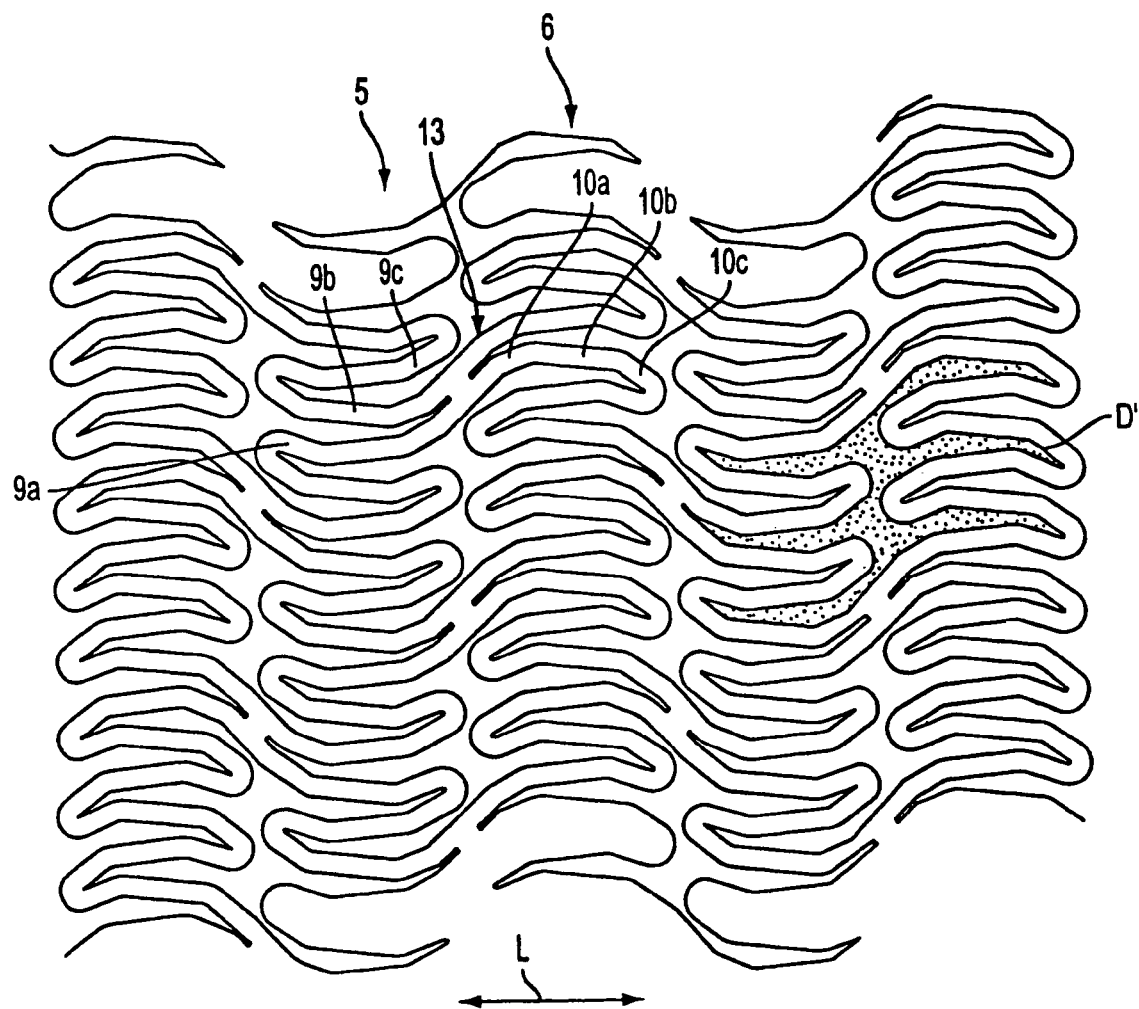
FIG. 5 is a schematic view of an alternative web structure of the stent of FIG. 1 having transition sections and shown in an as-manufactured configuration.

Referring now to FIG. 5, an alternative embodiment of the web structure of stent 1 is described. FIG. 5 shows the alternative web structure in an as-manufactured configuration. The basic pattern of the embodiment of FIG. 5 corresponds to that of the embodiment of FIGS. 2-4. Thus, this alternative embodiment also relates to a stent having a tubular flexible body with a wall having a web structure configured to expand from a contracted delivery configuration to the deployed configuration.

Likewise, the web structure again comprises a plurality of neighboring web patterns, of which two are illustratively labeled in FIG. 5 as web patterns 5 and 6. Web patterns 5 and 6 are again provided with adjoining webs 9 and 10, respectively. Each of webs 9 and 10 is subdivided into three sections, and reference is made to the discussion provided hereinabove, particularly with respect to FIG. 4. As will of course be understood by one of skill in the art, the stent of FIG. 5 will have a smaller diameter when contracted (or crimped) for delivery, and may have a larger diameter when illustrated in FIG. 5 when deployed (or expanded) in a vessel.

The embodiment of FIG. 5 differs from the previous embodiment by the absence of connection elements between web patterns. In FIG. 5, web patterns are interconnected to neighboring web patterns by transition sections 13, as shown by integral transition section 13 disposed between sections 9*c* and 10*c*. Symmetric, inverted web patterns are thereby obtained in the region of transition sections 13. To enhance stiffness, transition sections 13 preferably have a width greater than twice the width of webs 9 or 10.

As seen in FIG. 5, every third neighboring pair of webs 9 and 10 is joined by an integral transition section 13. As will be clear to those of skill in the art, the size and spacing of transition sections 13 may be altered in accordance with the principles of the present invention.

An advantage of the web structure of FIG. 5 is that it provides stent 1 with compact construction coupled with a high degree of flexibility in the delivery configuration and high load-bearing capabilities in the deployed configuration. Furthermore, FIG. 5 illustrates that, as with connection elements 7 and 8 of FIG. 4, transition sections 13 have an alternating orientation and are disposed obliquely relative to the longitudinal axis of the stent (shown by reference line L). FIG. 5 also illustrates that, especially in the deployed configuration, an H-like configuration of transition sections 13 with adjoining web sections is obtained.

The stent of FIG. 5 is well-suited for use as a balloon-expandable stent, and may be manufactured from stainless steel alloys. Unlike the stent of FIG. 4, which is formed in the contracted delivery configuration, the stent of FIG. 5 preferably is formed in a partially deployed configuration by removing the shaded areas D' between webs 9 and 10 using laser-cutting or chemical etching techniques. In this case, central sections 9*b* and 10*b* are substantially aligned with the longitudinal axis L of the stent when the stent is crimped onto the dilatation balloon of a delivery system.

Figure 6A:
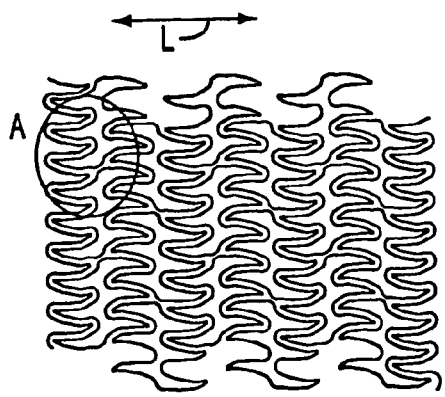
FIGS. 6A and 6B are, respectively, a schematic view and detailed view of an alternative embodiment of the web structure of FIG. 5.
Figure 6B:
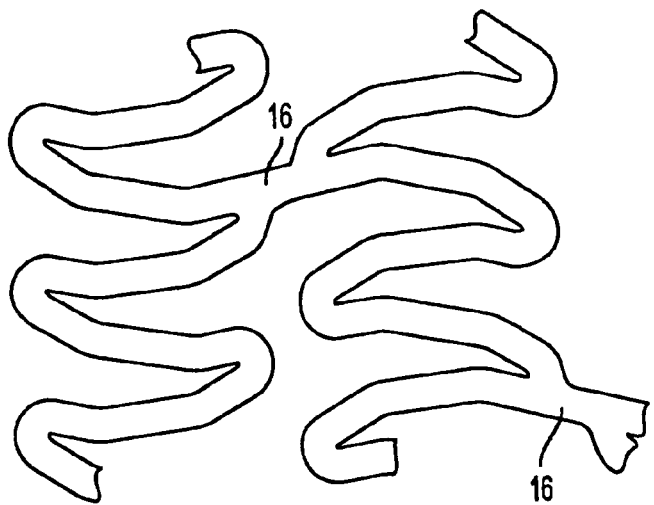

Referring now to FIGS. 6 and 7, alternative embodiments of the web structure of FIG. 5 are described. These web structures differ from the embodiment of FIG. 5 in the spacing of the transition sections. Web structure 15 of FIGS. 6A and 6B provides a spacing of transition sections 16 suited for use in the coronary arteries. FIG. 6A shows the overall arrangement, while FIG. 6B provides a detail view of region A of FIG. 6A. Other arrangements and spacings will be apparent to those of skill in the art and fall within the scope of the present invention.

Figure 7A:
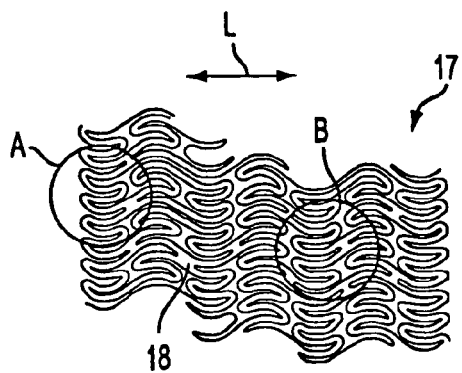
FIGS. 7A-7D are, respectively, schematic and detailed views of another alternative embodiment of the web structure of the stent of the present invention, and a cross-sectional view of the stent.
Figure 7B:
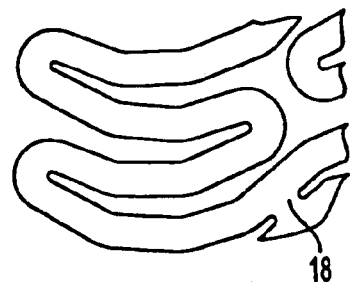
Figure 7D:
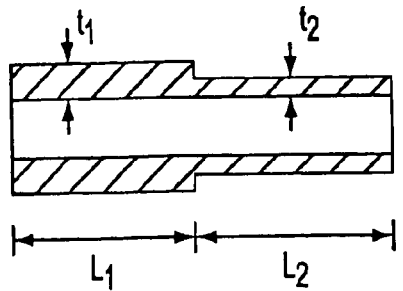
Figure 7C:
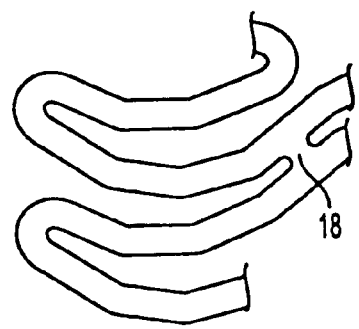

Web structure 17 of FIGS. 7A-7D provides stent 1 with a variable wall thickness and a distribution density or spacing of transition sections 16 suited for use in the renal arteries. FIG. 7A shows the arrangement of web structure 17 along the length of stent 1, and demonstrates the spacing of transition sections 18. FIGS. 7C and 7D provide detail views of regions A and B, respectively, of FIG. 7A, showing how the spacing and shape of the webs that make up web structure 17 change as stent 1 changes along its length. In particular, as depicted (not to scale) in FIG. 7D, stent 1 has first thickness $t_1$ for first length $L_1$ and second thickness $t_2$ for second length $L_2$.

The variation in thickness, rigidity and number of struts of the web along the length of the stent of FIGS. 7A-7D facilitates use of the stent in the renal arteries. For example, the thicker region $L_1$ includes more closely spaced and sturdier struts to provide a high degree of support in the ostial region, while the thinner region $L_2$ includes fewer and thinner struts to provide greater flexibility to enter the renal arteries. For such intended applications, region $L_1$ preferably has a length of about 6-8 mm and a nominal thickness $t_1$ of 0.21 mm, and region $L_2$ has a length of about 5 mm and a nominal thickness $t_2$ of about 0.15 mm.

As depicted in FIGS. 7A-7D, the reduction in wall thickness may occur as a step along the exterior of the stent, such as may be obtained by grinding or chemical etching. One of ordinary skill in the art will appreciate, however, that the variation in thickness may occur gradually along the length of the stent, and that the reduction in wall thickness could be achieved by alternatively removing material from the interior surface of the stent, or both the exterior and interior surfaces of the stent.

Figure 8A:
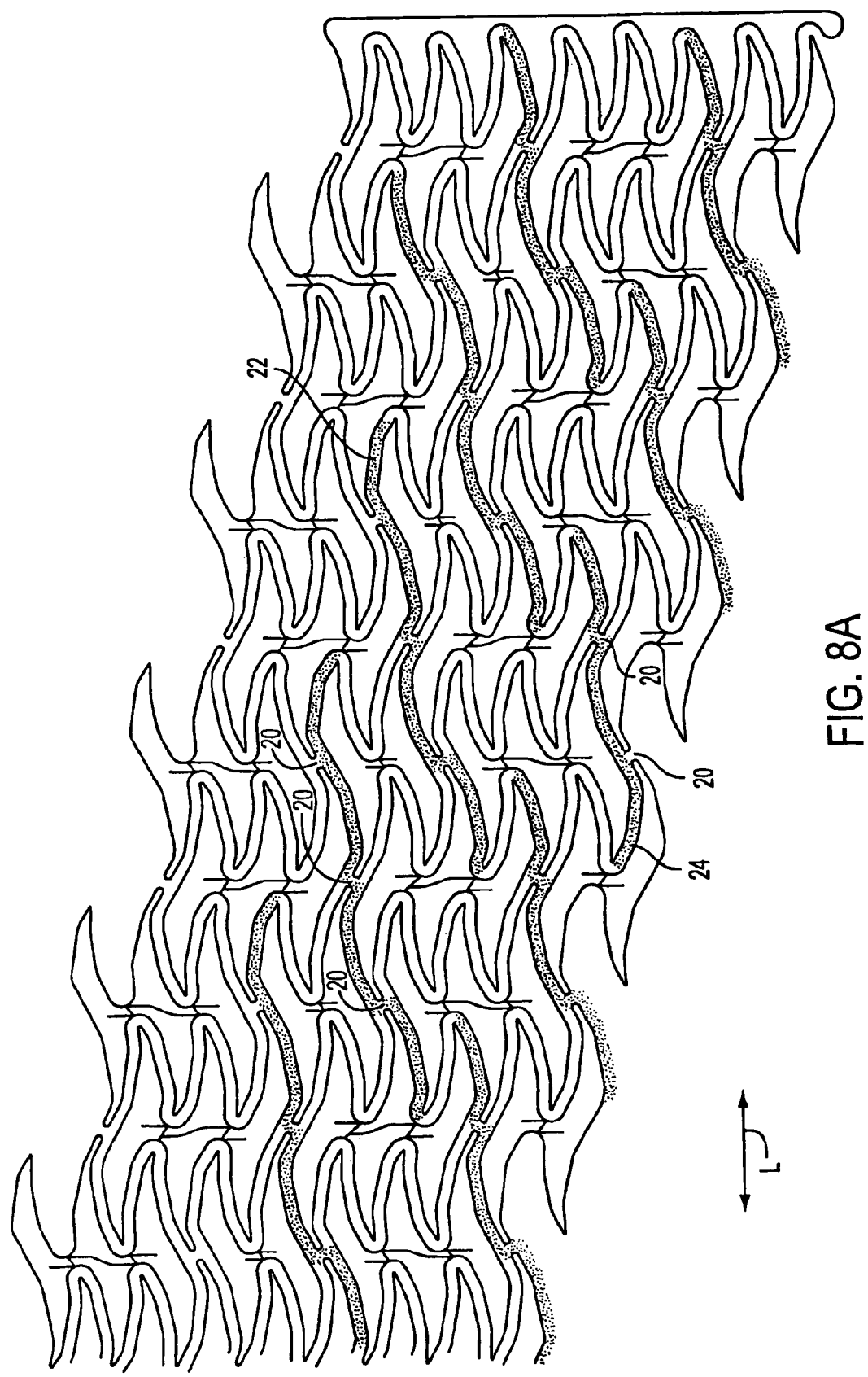
FIGS. 8A and 8B are views further alternative embodiments of the stent of the present application having different interconnection patterns.
Figure 8B:
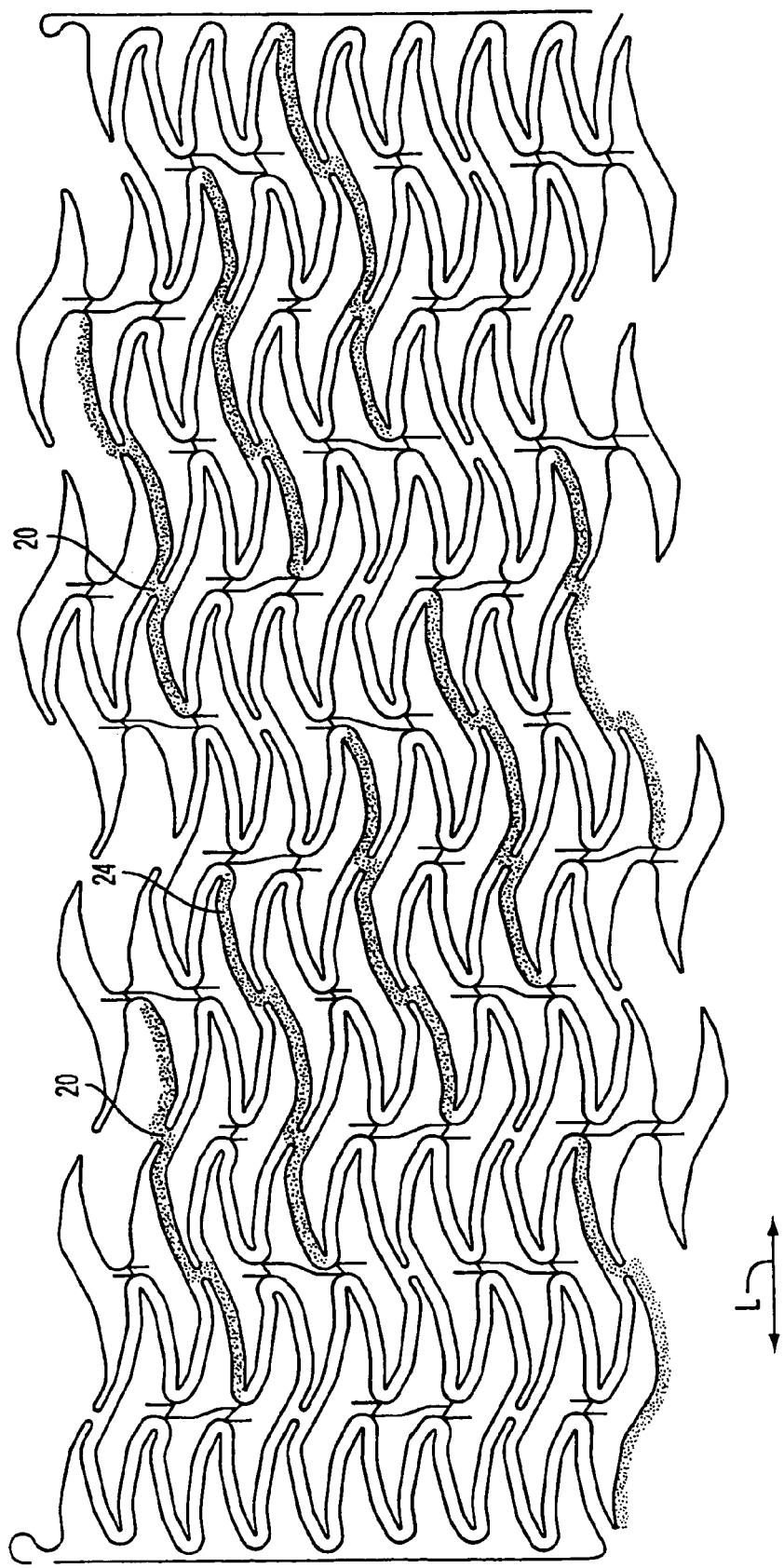

In FIGS. 8A and 8B, additional embodiments of web structures of the present invention, similar to FIG. 5, are described, in which line L indicates the direction of the longitudinal axis of the stent. In FIG. 5, every third neighboring pair of webs is joined by an integral transition section 13, and no set of struts 9a-9c or 10a-10c directly joins two transition sections 13. In the embodiment of FIG. 8A, however, integral transition sections 20 are arranged in a pattern so that the transition sections span either four or three adjacent webs. For example, the portion indicated as 22 in FIG. 8A includes three consecutively joined transition sections, spanning four webs. In the circumferential direction, portion 22 alternates with the portion indicated at 24, which includes two consecutive transition sections, spanning three webs.

By comparison, the web pattern depicted in FIG. 8B includes only portions 24 that repeat around the circumference of the stent, and span only three webs at a time. As will be apparent to one of ordinary skill, other arrangements of integral transition regions 13 may be employed, and may be selected on an empirical basis to provide any desired degree of flexibility and trackability in the contracted delivery configuration, and suitable radial strength in the deployed configuration.

Referring now to FIGS. 9A and 9B, a further alternative embodiment of the stent of FIG. 8B is described, in which the transition sections are formed with reduced thickness. Web structure 26 comprises transition sections 27 disposed between neighboring web patterns. Sections 27 are thinner and comprise less material than transition sections 20 of the embodiment of FIG. 8B, thereby enhancing flexibility without significant reduction in radial stiffness.

Figure 10A:
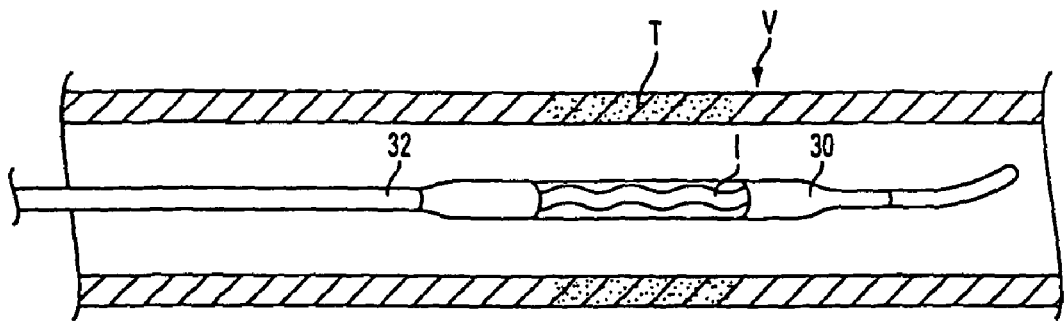
FIGS. 10A-10D illustrate a method of deploying a balloon expandable embodiment of a stent constructed in accordance with the present invention.

Referring now to FIGS. 10A-10D, a method of using a balloon expandable embodiment of stent 1 is provided. Stent 1 is disposed in a contracted delivery configuration over balloon 30 of balloon catheter 32. As seen in FIG. 10A, the distal end of catheter 32 is delivered to a target site T within a patient's vessel V using, for example, well-known percutaneous techniques. Stent 1 or portions of catheter 32 may be radiopaque to facilitate positioning within the vessel. Target site T may, for example, comprise a stenosed region of vessel V at which an angioplasty procedure has been conducted.

Figure 10B:
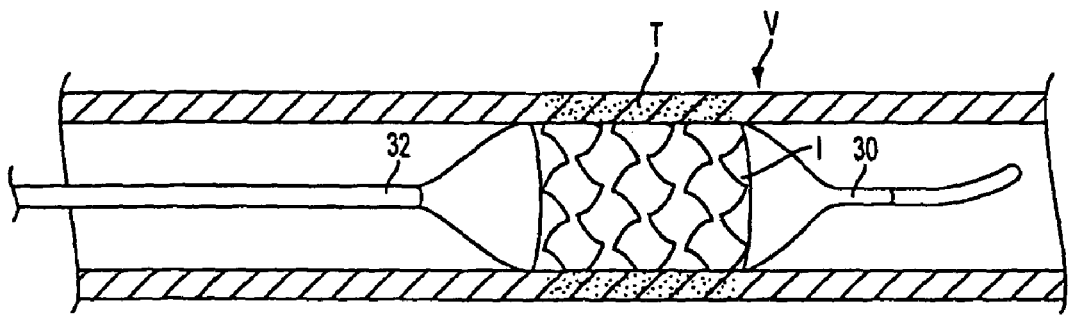
Figure 10C:
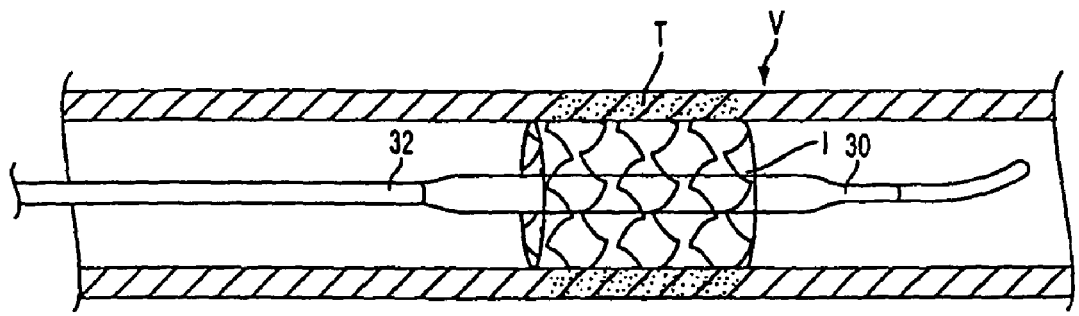
Figure 10D:
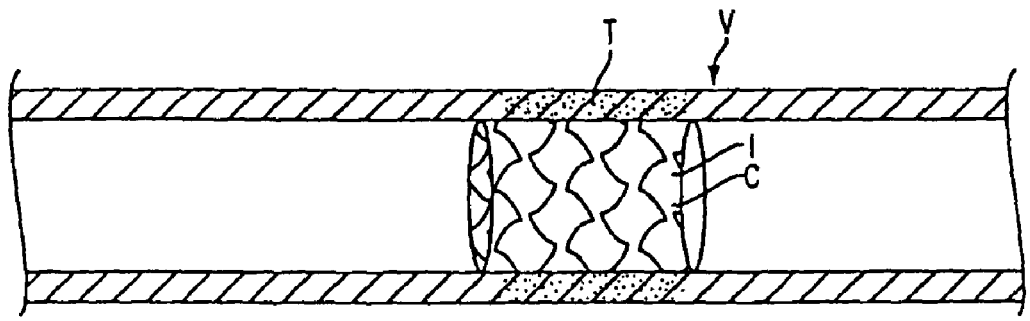

In FIG. 10B, balloon 30 is inflated to expand stent 1 to the deployed configuration in which it contacts the wall of vessel V at target site T. Notably, the web pattern of stent 1 described hereinabove minimizes a length decrease of stent 1 during expansion, thereby ensuring that stent 1 covers all of target site T. Balloon 30 is then deflated, as seen in FIG. 10C, and balloon catheter 32 is removed from vessel V, as seen in FIG. 10D.

Stent 1 is left in place within the vessel. Its web structure provides radial stiffness that maintains stent 1 in the expanded configuration and minimizes restenosis. Stent 1 may also comprise external coating C configured to retard restenosis or thrombosis formation around the stent. Coating C may alternatively deliver therapeutic agents into the patient's blood stream.

Although preferred illustrative embodiments of the present invention are described hereinabove, it will be evident to one skilled in the art that various changes and modifications may be made therein without departing from the invention. It is intended in the appended claims to cover all such changes and modifications that fall within the true spirit and scope of the invention.

What is claimed is:

1. A system for supporting a body lumen, the system comprising:
    a tubular body having a longitudinal axis, and having proximal and distal ends and a lumen extending longitudinally therebetween, and a wall having areas thereof that define a web structure configured for circumferential expansion from a contracted delivery configuration to an expanded deployed configuration;
    the web structure comprising a plurality of web patterns interconnected with one another at a plurality of transition sections, and that are arranged so that the web patterns are situated side-by-side along the longitudinal length of the tubular body, with each web pattern also extending circumferentially around the wall;
    at least one of said interconnected web patterns comprising,
        at least three webs joined end-to-end so as to extend between a pair of transition sections with no other transition sections between the pair of transition sections;
        said three webs that are joined end-to-end being joined by two bends so that the bends permit the three webs to be generally foldable between the pair of transition sections when said tubular body is in the contracted delivery configuration, and then unfolded when said tubular body is expanded to the deployed configuration; and
        said at least three webs each comprising a plurality of web sections, with one of the web sections being angled relative to one other web section when the stent is in the expanded deployed configuration; and
    a catheter configured to accept the tubular body in the contracted delivery configuration, the catheter configured to deliver the tubular body intravascularly and to transition the tubular body from the contracted delivery configuration to the expanded deployed configuration.

2. The system of claim 1, wherein the catheter comprises a balloon catheter.

3. The system of claim 2, wherein the tubular body is compressed on to a balloon of the balloon catheter.

4. The system of claim 1, wherein each circumferential pair of transition sections is separated by at least three webs.

5. The system of claim 1, wherein at least some transition sections of the tubular body define an H-shaped structure.

6. The system of claim 5, wherein at least some of the arcuate webs of the tubular body span two H-shaped structures.

7. The system of claim 5, wherein at least one of the H-shaped structures is disposed at an angle relative to a longitudinal axis of the tubular body.

8. The system of claim 1, wherein each web comprises three web sections, with one of the sections being a central section joined at opposite ends thereof to two lateral sections, with at least one of the three web sections comprising a substantially straight section.

9. The system of claim 8, wherein each web comprises three substantially straight sections, and wherein each of the lateral sections is angled relative to the central section when the stent is expanded, with each angle being expandable when the webs are unfolded to place the stent in the expanded deployed configuration.

10. The system of claim 1, wherein the at least three webs are joined end-to-end in a manner that defines an S-shaped structure between the two and only two transition sections.

11. The system of claim 1, wherein the tubular body comprises a deformable material.

12. A system for supporting a body lumen, the system comprising:
   a tubular body having a longitudinal axis, and having proximal and distal ends and a lumen extending longitudinally therebetween, and a wall having areas thereof that define a web structure configured for circumferential expansion from a contracted delivery configuration to an expanded deployed configuration;
   the web structure comprising a plurality of web patterns interconnected with one another at a plurality of transition sections, and that are arranged so that the web patterns are situated side-by-side along the longitudinal length of the tubular body, with each web pattern also extending circumferentially around the wall;
   at least one of said interconnected web patterns comprising,
      at least three webs joined end-to-end so as to extend between a pair of transition sections with no intervening transition sections between the pair of transition sections;
      said three webs that are joined end-to-end being joined by two bends so that the bends permit the three webs to be generally foldable between the pair of transition sections when said tubular body is in the contracted delivery configuration, and then unfolded when said tubular body is expanded to the deployed configuration;
      each web comprising three web sections, with one of the web sections being a central section joined at opposite ends thereof to two lateral sections, each of the lateral sections being angled relative to the central section when the stent is in the expanded deployed configuration; and
   a catheter configured to accept the stent in the delivery configuration, the catheter configured to deliver the stent intravascularly and to transition the stent from the contracted delivery configuration to the expanded deployed configuration.

13. The system of claim 12, wherein the catheter comprises a balloon catheter.

14. The system of claim 13, wherein the stent is compressed on to a balloon of the balloon catheter.

15. The system of claim 12, wherein each transition section is separated, around the circumference of the wall, by at least five webs joined end-to-end by four bends.

16. The system of claim 15, wherein each of the three web sections are substantially straight sections, and wherein each of the lateral sections is angled relative to the central section when the stent is expanded, with each angle being expandable when the webs are unfolded to place the stent in the expanded deployed configuration.

17. The system of claim 12, wherein the transition sections of the stent define H-shaped structures.

18. The system of claim 17, wherein at least one of the H-shaped structures of the stent is disposed at an angle relative to a longitudinal axis.

19. The system of claim 12, wherein at least some of the arcuate webs of the stent span two H-shaped structures.

20. The system of claim 12, wherein at least one of the three web sections comprises a substantially straight section.

21. The system of claim 12, wherein the five webs are joined end-to-end in a manner that defines an S-shaped structure.

22. The system of claim 12, wherein the stent comprises a deformable material.

* * * * *